United States Patent [19]

Hermecz et al.

[11] 4,260,612
[45] Apr. 7, 1981

[54] ANTIALLERGIC NITROGEN BRIDGE-HEAD COMPOUNDS

[75] Inventors: István Hermecz; Zoltan Meszáros; Tibor Breining; Sándor Virag; Lelle Vasvári née Debreczi; Ágnes Horváth; Gábor Nagy; Attila Mándi; Tamás Szüts; István Bitteer; Gyula Sebestyén, all of Budapest, Hungary

[73] Assignee: Chinoin Gyógyszer és Vecyeszeti Termekek Gyara Rt., Budapest, Hungary

[21] Appl. No.: 967,957

[22] Filed: Dec. 11, 1978

[30] Foreign Application Priority Data

Dec. 29, 1977 [HU] Hungary .............. CI 1795

[51] Int. Cl.³ .................. A61K 31/505; C07D 471/04
[52] U.S. Cl. .................... 424/251; 542/422; 542/439; 544/116; 544/119; 544/252; 544/282; 424/248.53; 424/248.56
[58] Field of Search ............... 544/282, 116, 119, 252; 424/251; 542/422, 439

[56] References Cited

U.S. PATENT DOCUMENTS

| | | | |
|---|---|---|---|
| 2,786,056 | 3/1957 | Sletzinger et al. | 542/422 X |
| 3,560,502 | 2/1971 | Davoll | 542/422 X |
| 3,563,981 | 2/1971 | Lesher | 260/240.3 |
| 3,585,198 | 6/1971 | Meszaros et al. | 544/282 |
| 3,642,797 | 2/1972 | Lesher | 544/282 |
| 4,122,274 | 10/1978 | Juby | 544/282 |
| 4,123,533 | 10/1978 | Hermecz et al. | 424/251 |

OTHER PUBLICATIONS

Morisawa, et al., Chemical Abstracts, vol. 85, 21, 423K, (1976).
Noller, Chemistry of Organic Compounds, 3rd ed., W. B. Saunders Co., Philadelphia, (1965), pp. 253–254, 514, 516–517, 597, 676.
Macarovici, et al., Chemical Abstracts, vol. 61, 9371h (1964).

Primary Examiner—Donald G. Daus
Assistant Examiner—Diana G. Rivers
Attorney, Agent, or Firm—Karl F. Ross

[57] ABSTRACT

Antiallergic and antiasthmatic compounds of the formula

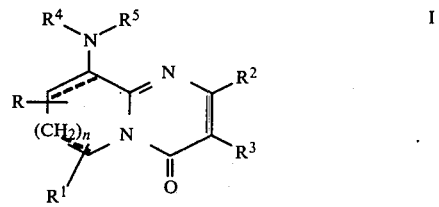

of which 9-phenylamino-6-methyl-4-oxo-6,7-dihydro-4H-pyrido(1,2-a)pyrimidine-3-carboxylic acid and optically active antipodes and salts thereof are examples.

8 Claims, No Drawings

ANTIALLERGIC NITROGEN BRIDGE-HEAD COMPOUNDS

The present invention relates to new nitrogen bridgehead condensed pyrimidine compounds, to a process for the preparation thereof and to pharmaceutical compositions containing same. The new compounds may be used in therapy mainly as antiallergic or antiasthmatic compositions.

It is known, that pyrido(1,2-a)pyrimidine derivatives have valuable analgesic and other CNS influencing activities (British Patent Specification No. 1,209,946). The most effective representative of the compounds of this reference is the analgesic 1,6-dimethyl-3-ethoxycarbonyl-6-methyl-4-oxo-4H-pyrido(1,2-a)pyridinium-methosulfate (PROBON®, Rimazolium) (Arzneimittelforschung 22, 815, 1972). The pyrido(1,2-a)pyrimidine derivatives are prepared by the ring closure of the suitable (2-pyridyl-amino-methylene)malonic acid dialkyl esters. Other pyrido(1,2-a)pyrimidine derivatives have been disclosed in British Patent Specification No. 1,454,312.

The present invention relates to new compounds of the formula

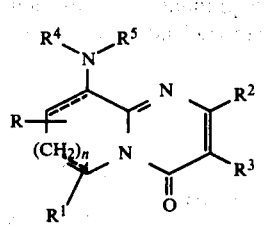

salts, hydrates and stereoisomers, geometric isomers and tautomers thereof, wherein
the upper broken line stands for an optionally present carbon-carbon bond,
R is hydrogen or $C_{1-4}$ alkyl,
$R^1$ is hydrogen or $C_{1-4}$ alkyl, styryl or carboxy or a derivative thereof, or
R and $R^1$ together form $-(CH=CH)_2$, when the lower broken line forms a further C—C bond and in every other case a single bond is present in the 6,7-position,
$R^2$ is hydrogen, $C_{1-4}$ alkyl or hydroxy,
$R^3$ is hydrogen, $C_{1-4}$ alkyl, aryl, $C_{1-4}$ alkanoyl, carboxy or a derivative thereof or a $-(CH_2)_m-COOH$ or a derivative thereof on the carboxy group, and m=1, 2 or 3,
$R^4$ is hydrogen, $C_{1-4}$ alkyl which can be substituted by hydroxy or carboxy, trifluoromethyl, substituted or unsubstituted $C_{6-10}$ aryl, phenyl-$(C_{1-3})$-alkyl or a substituted or unsubstituted heterocycle,
$R^5$ is hydrogen, $C_{1-4}$ alkyl, $C_{6-10}$ aryl, phenyl-$C_{1-4}$ alkyl, alkanoyl containing $C_{1-4}$ alkyl or substituted or unsubstituted benzoyl or heteroaroyl or
$R^4$ and $R^5$ together with the nitrogen to which they are attached form a piperidino, pyrrolidino or morpholino ring or
$R^4$ and $R^5$ together with the adjacent nitrogen to which they are attached form a group of the general formula $-N=C(R^6R^7)$, where $R^6$ is hydrogen and $R^7$ is substituted or unsubstituted phenyl, and n=1.

The term "lower alkyl" as used hereinafter for alkyl groups or alkyl containing groups, such as alkoxy, is $C_{1-6}$, preferably $C_{1-4}$, straight or branched aliphatic saturated hydrocarbons, such as methyl, ethyl, n-propyl, isopropyl, n-butyl, secondary-butyl, tertiary-butyl, n-pentyl, neo-pentyl, n-hexyl.

The term "derivative of the carboxyl group" means the usual carboxylic acid derivatives, such as lower alkoxycarbonyl, aryloxycarbonyl, aralkoxycarbonyl or other esters a, carbamoyl group which can be substituted with one or two lower alkyl, aryl or aralkyl; the carboxylic acid derivatives also can be cyano, carboxylic acid hydrazido or hydroxamic acid (—CO—N-HOH).

The term "aryl" used as such or in aryl containing groups such as aryloxy, means substituted or unsubstituted $C_6$ and $C_{10}$ aromatic groups, such as phenyl or naphthyl or substituted derivatives thereof.

The term "aralkyl" used as such or in aralkyl containing groups, such as aralkyloxy, means $C_{1-3}$-alkyl substituted with phenyl or naphthyl, such as benzyl, beta-phenyl-ethyl, alpha,beta-diphenyl-ethyl, beta,beta-diphenyl-ethyl.

The term "substituted alkyl" means alkyl substituted with hydroxy, halogen, carboxy or carboxylic acid derivatives as defined, amino, substituted amino, alkoxy, or alkanoyloxy, such as trifluoromethyl, hydroxyethyl, aminoethyl, carboxymethyl, and beta-carboxyethyl.

The term "lower alkanoyl" as used herein means groups containing 1 to 4 carbon atoms in the alkyl group, preferably alkane carboxylic acid radicals, such as formyl, acetyl, propionyl and butyryl.

The term "aroyl" indicates acid radicals of aromatic carboxylic acids, such as optionally substituted benzoic acid.

The term "heteroaroyl" means heterocyclic carboxylic acid radicals, such as pyridine-2-, -3- or -4-carboxylic acid, furan-carboxylic acid.

The term "heterocyclic group" means mono- or bicyclic rings containing 1 to 4 nitrogen, oxygen and/or sulfur atoms, being optionally substituted or partially or completely saturated rings, such as thienyl, furyl, pyrrolyl, pyridyl, pyrimidinyl, pyrazinyl, pyridazinyl, quinolyl, isoquinolyl, benzofuranyl, benzooxazolyl, oxazolyl, oxadiazolyl, imidazolyl, benzimidazolyl, indolyl, benzothiazolyl, benzisothiazolyl, tetrazolyl, thiadiazolyl, triazinyl, piperidinyl, morpholinyl, pyrrolidinyl, piperazinyl, N-methylpiperazinyl.

The term "heteroaryl" used hereinafter stands for a mono- or bicyclic optionally substituted aromatic ring-system containing 1 to 4 nitrogen, oxygen and/or sulfur atoms, such as thienyl, furyl, pyrrolyl, pyridyl, pyrimidinyl, pyrazinyl, pyridazinyl, quinolyl, isoquinolyl, benzofuranyl, benzoxazolyl, oxazolyl, oxadiazolyl, imidazolyl, benzimidazolyl, indolyl, benzothiazolyl, benzisothiazolyl, tetrazolyl, thiadiazolyl, triazinyl.

The aryl groups, the aryl group of the aralkyl groups and the heterocyclic groups can be substituted with one or more groups or atoms, such as halogen (such as chlorine, bromine, iodine or fluorine), lower alkyl (such as methyl, ethyl), lower alkoxy (such as methoxy, ethoxy), lower alkylenedioxy (methylenedioxy, ethylenedioxy or propylenedioxy), mono-, di- or trihalogenalkyl (such as trifluoromethyl), amino, alkanoylamino, substituted amino, carboxy or carboxylic acid derivatives, sulfonic acid or a salt or ester thereof, hydroxy, alkanoyloxy, aroyloxy, heteroaroyloxy, nitro, mercapto, and lower alkylthio.

Preferred representatives of the new compounds are those derivatives—wherein

R is hydrogen,

R¹ represents hydrogen, lower alkyl (preferably methyl), styryl or lower alkoxycarbonyl (preferably methoxycarbonyl or ethoxycarbonyl), R² is hydrogen, lower alkyl (such as methyl) or hydroxy, R³ is carboxy, lower alkoxycarbonyl (preferably methoxycarbonyl, ethoxycarbonyl), carbamoyl, cyano, formyl, lower alkyl (preferably methyl) or phenyl, R⁴ is hydrogen, lower alkyl (preferably methyl), hydroxyethyl, carboxyalkyl, preferably substituted phenyl or naphthyl, trifluoromethyl, benzyl, 2-, 3- or 4-pyridyl, benzothiazol-2-yl, methoxycarbonyl or ethoxycarbonyl, R⁵ is halogen, lower alkanoyl (preferably acetyl), benzoyl or nicotinoyl or —NR⁴R⁵ is piperidinyl, pyrrolidinyl, morpholinyl or
—N=CR⁶R⁷, wherein R⁶ is hydrogen and R⁷ is optionally substituted phenyl, n=0 or 1.

R⁴ stands particularly for phenyl, bearing optionally one, two or three substituents in o-, m- and/or p-position, selected from hydroxy, halogen, lower alkyl, sulfonic acid, carboxy or carboxylic acid derivatives, alkoxy, alkylenedioxy, amino, substituted amino, nitro and trifluoromethyl. Particularly favourable properties are shown by those compounds of the formula I—wherein R is hydrogen, R¹ represents 6-methyl, R² is hydrogen, R³ is carboxy, R⁴ is optionally substituted phenyl, R⁵ is hydrogen, n=1—and pharmaceutically effective salts thereof.

Also where R⁴ stands particularly for substituted phenylor naphthyl the substituents include hydroxy, C₁ to C₄ alkoxy, nitro, carboxy, C₁ to C₄ alkyl, trifluoromethyl, amino or halogen.

The compounds of the formula I form salts with pharmaceutically acceptable organic and inorganic acids. Hydrochlorides, hydrobromides, hydroiodides, sulfates, nitrates, phosphates, maleates, malates, succinates, acetates, tartrates, lactates, fumarates, or citrates can be formed.

Compounds of the formula I containing carboxy or sulfonic acid groups form salts with pharmaceutically acceptable bases, such as alkali metal salts, such as sodium or potassium salts, alkaline earth metal salts, such as calcium or magnesium salts, ammonium salts and salts with organic amines, such as triethylamine salts, ethanolamine salts, etc.

The invention includes optical and geometrical isomers and tautomers of the compounds of the formula I as well. The structure of geometric isomers are shown by the formulae

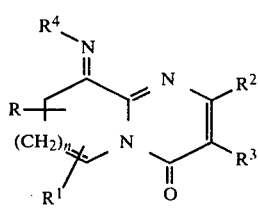
IA and

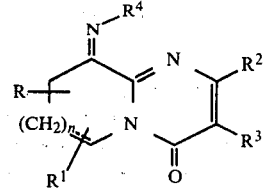
IB (R⁵ = hydrogen)

The structure of the tautomers is shown by reaction scheme A:

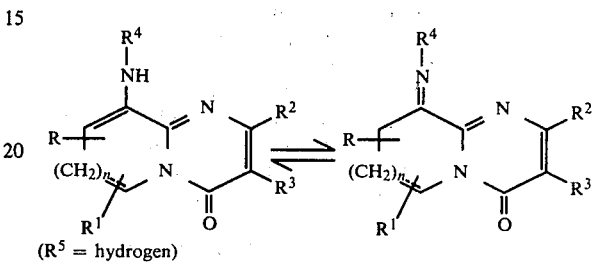

(R⁵ = hydrogen)

In preparing compounds of the formula I containing hydroxy as R² keto-enol tautomery shown in reaction scheme B:

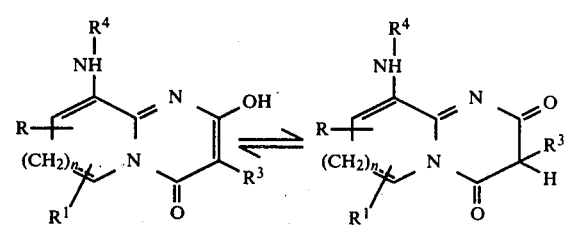

can also occur.

The new compounds of the formula I, pharmaceutically acceptable salts thereof, hydrates, optically active, geometric and stereoisomers and tautomers thereof may be prepared by (a) reacting a compound of the formula

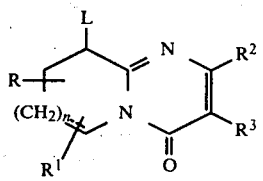
II

—wherein R, R¹, R², R³, n and the dotted line are as defined above, and L is a leaving group—with a compound of the formula

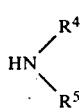
III

—wherein R⁴ and R⁵ are as defined above—and if desired oxidizing the formed product without isolation or after isolation or (b) reacting a compound of the formula

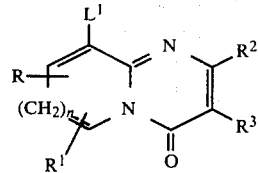

—wherein R, $R^1$, $R^2$, $R^3$, n and the dotted line are as defined above and $L^1$ is a leaving group—or a tautomer thereof with a compound of the general formula III—wherein $R^4$ and $R^5$ are as given above—and subjecting, if desired a compound of the formula I thus obtained to one or more conversions, i.e. converting $R^1$, $R^2$, $R^3$, $R^4$ and/or $R^5$ into another $R^1$, $R^2$, $R^3$, $R^4$ and/or $R^5$ by methods known per se, converting a compound of the formula I containing an acid group into a salt by reacting it with a pharmaceutically acceptable base, converting a basic compound of the formula I into an acid-addition salt by reacting it with a pharmaceutically acceptable acid, setting free a compound of the formula I from its salt formed with an acid or a base, separating a racemate of the general formula I into its optically active antipodes.

In compounds of formula II used as starting materials in process variant (a) L stands for a conventionally used leaving group, such as halogen, such as chlorine or bromine, alkylsulfonyloxy, such as methane-sulfonyloxy, optionally substituted arylsulfonyloxy, such as p-toluene-sulfonyloxy or p-bromo-phenyl-sulfonyloxy or alkanoyloxy, such as acetoxy. The reaction of compounds of the formulae II and III is preferably conducted in the presence of an acid-binding agents. As acid-binding agents, preferably alkali metal carbonates, such as sodium or potassium carbonate, alkali metal hydrogen carbonates, such as sodium or potassium hydrogen carbonate, alkali metal salts of weak acids, such as sodium acetate or an excess of the starting material of the formula III can be employed. The reaction may be carried out in an inert solvent. As the reaction medium preferably aromatic hydrocarbons, such as benzene, toluene, xylene, esters, such ethyl acetate, alcohols, such as methanol, ethanol or dimethylformamide are used. The reaction is preferably carried out at 0°–200° C., preferably at room temperature or under heating at the boiling point of the reaction mixture.

Presumably compounds of the formula

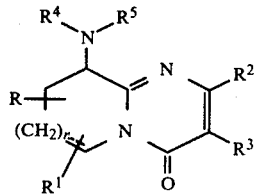

are formed in the reaction as intermediate compounds—wherein R, $R^1$, $R^2$, $R^3$, $R^4$, $R^5$, n and the broken line are as defined above. These intermediates if desired may be oxidized after isolation or without isolation. The intermediate product is preferably not isolated and the reaction mixture is subjected to the oxygen of the air at room temperature or under heating followed by oxidation.

According to process variant (b) of the present invention a compound of the formula IV is reacted with a compound of the formula III. In the compound of the formula IV, $L^1$ may be a conventional leaving group, such as halogen, such as chlorine or bromine, alkylsulfonyloxy, such as methanesulfonyloxy, optionally substituted arylsulfonyloxy, such as p-toluenesulfonyloxy or p-bromo-phenylsulfonyloxy, alkanoyloxy, such as acetoxy or hydroxy. The reaction can be carried out in the presence of an acid-binding agent. As acid-binding agents preferably alkali metal hydrogencarbonates, such as sodium or potassium hydrogencarbonate, alkali metal salts of weak organic acids, such as sodium acetate or an excess of the compound of the formula III may be employed. The reaction may be carried out in an inert solvent. As reaction media aromatic hydrocarbons, such as benzene, toluene, xylene, esters, such as ethyl acetate may be employed. The reaction is preferably carried out at 0°–200° C., preferably at room temperature or with heating, e.g. at the boiling point of the reaction mixture. When using compounds of the formula IV containing hydroxyl as $L^1$ as starting materials the reaction is preferably performed in the presence of a water binding agent, such as dicyclohexylcarbodiimide.

The compounds of the formula I obtained in the processes mentioned above may be isolated from the reaction mixture by methods known per se. The compound of the formula I precipitates from the reaction mixture in many cases in the form of a salt or hydrate thereof and may be separated by filtration or centrifuging. When the reaction is carried out in an aqueous medium the end product may be isolated from the reaction mixture by shaking out with a suitable organic solvent, such as benzene, chloroform, ether and by evaporation of the organic solvent extract. When the reaction is carried out in an organic solvent the compound of the formula I may be separated from the reaction mixture by removing the organic solvent. The obtained compound of the formula I may be purified, if desired, by recrystallization or by chromatography.

A compound of the formula I thus obtained may be converted, if desired, to another compound of the formula I by methods known per se. The conversion may take place at groups $R^1$, $R^3$, $R^4$, or $R^5$. The additional conversions may be conducted by methods and under circumstances known per se.

A carboxy group at $R^1$, $R^3$ or $R^4$ or $R^5$ may be converted to alkoxycarbonyl, aryloxycarbonyl or aralkyloxycarbonyl by esterification by methods known per se. The esterification may be carried out by reaction with a suitable alcohol or phenol in the presence of an acid catalyst (such as conc. sulfuric acid) or by treatment with a diazoalkane, such as diazomethane, diazoethane.

A derivative containing carboxy may be decarboxylated by heating and thus a suitable derivative containing hydrogen in the place of carboxy is obtained. The decarboxylation may preferably be carried out in the presence of an acid (such as phosphoric acid). A derivative containing carboxy may optionally be converted to substituted acid amide by reaction with an amine. The preparation of the substituted acid amides may be carried out through an active ester, such as active ester formed with a chloroformic acid ethyl ester by methods known per se.

The ester group at $R^1$, or $R^3$ or $R^4$ or $R^5$ may be reesterified by heating with a suitable alcohol in half excess amount to give another ester. An ester of the formula I may be treated with an acid or alkali to give a carboxylic acid of the formula I. The alkaline hydrolysis may be carried out with an alkali metalhydroxide in aqueous or alkanol medium by heating and the acid is set free from the forming alkali metal salt by acidifying. The hydrolysis carried out with a mineral acid gives directly a free carboxylic acid. The ester of the formula I is reacted with ammonia in an aqueous alcoholic medium to yield a suitable acid amide of the formula I or by reacting it with an optionally substituted hydrazine (such as hydrazine, methyl or phenyl hydrazine) a suitable hydrazide of the formula I is obtained.

A compound containing cyano at $R^1$ or $R^3$ or $R^4$ or $R^5$ of the formula I can be converted to a suitable carboxylic acid of the formula I by heating it in conc. sulfuric acid or conc. hydrochloric acid or conc. alkali metal hydroxide or to a suitable acid amide of the general formula I by a cold acid hydrolysis or alkaline hydrolysis latter being carried out at about 50° C. The alkaline hydrolysis is preferably carried out in the presence of hydrogen peroxide.

An acid amide of the formula I containing a carbamoyl at $R^1$ or $R^3$ or $R^4$ or $R^5$ can be heated in alkaline or acid medium to obtain a suitable carboxylic acid of the formula I. The hydrolysis of acid amides which do not hydrolize may readily be performed in the presence of nitric acid.

A carboxylic acid hydrazide of the formula I can be hydrolyzed to a carboxylic acid of the formula I by alkaline or acid hydrolysis. A compound of the formula I containing hydrogen as $R^5$ may be acylated to a compound of the formula I containing formyl, alkanoyl, aroyl or heteroaroyl at $R^5$. The acylation can be carried out with a suitable carboxylic acid or reactive derivative thereof by methods known per se. As acylating agents preferably acid halides, such as acid chlorides, acid anhydrides, active esters, such as pentachlorophenylesters may be used. The acylation may preferably be carried out in the presence of acid-binding agents, such as triethylamine. Acylation carried out with a free acid is preferably performed in the presence of a water-binding agent, such as dicyclohexylcarbodiimide. The acylation can be carried out by using acylating agents and methods known from the peptide chemistry.

A compound of the formula I containing hydrogen at $R^4$ and $R^5$ can be condensed with an aldehyde to convert a compound of the formula I containing $-NR^4R^5$ to a compound of the formula I containing $-N=CR^6R^7$. The condensation is carried out in an inert solvent (such as benzene or toluene) at room temperature or under heating. The water formed in the reaction is removed in the form of an azeotrope or bound by water-abstracting agent. As an aldehyde for example acetaldehyde or benzaldehyde is used.

Aryl at $R^4$ and/or $R^5$ may be subjected to one or more known conversions. Thus for example a compound of the formula I containing an unsubstituted phenyl group in place of $R^4$ and/or $R^5$ may be nitrated with a nitric acid-sulfuric acid mixture under cooling and the obtained nitro derivative may be reduced, if desired (e.g. by catalytic reduction) and the amino derivative may be alkylated or acylated, if desired.

The additional conversions carried out as mentioned above are also the subject of the present invention.

The obtained compound of the general formula I is set free from a salt formed with an acid or base by methods known per se.

An obtained basic compound of the formula I may be converted to an acid-addition salt formed with an inorganic or organic acid. The salt may be formed by methods known per se, by reacting a suitable compound of the formula I with a molar equivalent or excess of an acid in an inert organic solvent.

The compounds of the formula I having an acid group, such as carboxyl or sulfonic acid group, may be reacted with a suitable base, such as alkali metal hydroxides, alkaline-earth metal hydroxides, organic amines by methods known per se in order to obtain salts.

Compounds of the formula I having a different group from hydrogen at R and/or $R^1$ contain an asymmetry center and can be obtained in the form of optically active antipodes or racemates. The optically active antipodes of the compounds of the formula I can be formed by using an optically active compound of the formula II or IV in the process variants (a) and (b) or by resolving a racemic compound of the formula I. The resolution is carried out by methods known per se. The carboxyl-containing compound of the formula I can be resolved by reacting the racemate with a suitable optically active base (for example optically active threo-1-(p-nitro-phenyl)2-amino-propane-1,3-diol) and separating the formed members of the diastereomer salt-pair based on their different physical properties, for example by crystallization and setting free the optically active antipode from the salt by reacting it with a strong base.

The nitrogen bridgehead starting materials of the formula II and IV can be prepared by known methods, e.g. according to Arzneimittelforschung 22, 815, 1972. Compounds of the formula II can be prepared by halogenation and compounds of the formula IV e.g. by hydrolysis of compounds of the formula I.

The compounds of the formula I have anti-inflammatory, analgesic, thrombus-aggregation-inhibiting, anti-athereogenic, heart function and circulation regulating, tranquillizing, CNS-influencing, PG-antagonistic, anti-ulcer, antibacterial and antifungal activity and can be used in the human and veterinary therapy. The anti-allergic and anti-asthmatic activity of the compounds of the formula I is particularly outstanding.

The allergic reactions induced by the antigen-antibody interaction can occur in different tissues and organs accompanied by different symptoms. Most frequent form of allergy is asthma. An antiasthmatic agent disodium chromoglycate (1,3-bis-(2-carboxy-chromon-6-yl-ox)-2-hydroxy-propane, Intal[4]) is widely used, but is not active orally and produces the desired effect only by using a spinhaler, which makes the administration rather complicated. We have now found that the new compounds of the formula I cure the allergic symptoms both orally and intravenously and by administration by inspiration.

The efficiency of the compounds of the formula I was proved by standard tests to determine antiallergic activity. The tests were carried out by the PCA test-method (Ovary: J. Immun. 81, 355, 1958) and the Church-test (British J. Pharm. 46, 56–66, 1972; Immunology 29, 527–534, 1975) and as comparing substance disodium chromoglycate is used. The test is carried out in rats. The results obtained in PCA test are summarized in Table I.

The compound prepared according to Example 1 gives in the PCA test in a single i.v. dose of 320 μmole/kg. a percental activity of 100% while in a single i.v. dose of 10 μmole/kg. 60%. Released histamine in vitro, $ED_{50} = 12.3$ μmole/L.

TABLE I

| Compound | Test PCA test ED$_{50}$ μM/kg i.v. |
|---|---|
| 9-Phenylamino-6-methyl-4-oxo-6,7-dihydro-4H-pyrido[1,2-a]pyrimidine-3-carboxylic acid | 1.3 |
| disodium chromoglycolate | 1.0 |

The above data show that the representative of the new compounds of the general formula I exhibit oral activity as well, whereas disodium chromoglycolate is effective only when administered intravenously. Compounds of the formula I are more active also when being administered i.v.

The toxicity of the compounds of the general formula I is low, generally LD$_{50}$ > 500 mg/kg. p.o. in rats and mice.

The compounds of the formula I may be employed in the form of pharmaceutical compositions containing an active ingredient and inert solid or liquid organic or inorganic carriers. The compositions are prepared by methods known per se.

The compositions can be formulated in a form suitable for oral, parenteral administration or for inspiration, such as tablets, dragee, capsules, lozenges, powder mixture, aerosol spray, aqueous suspension or solution, solution to be injected or syrup. The compositions may contain suitable solid diluents or carriers, sterilizing aqueous solvent, non-toxic organic solvent. To the compositions suitable for oral administration the usual flavouring or sweetening agents may be added.

As carriers for the tablets suitable for oral administration preferably lactose, sodium citrate, calcium carbonate and disintegrating substances, such as starch, alginic acid, lubricants, such as talcum, sodium lauryl sulfate, magnesium stearate, may be used. The carrier of the capsules may be lactose and polyethylene glycol. The aqueous suspensions may contain emulsifying and suspending agents. A diluent of the organic solvent suspension may be selected from ethanol, glycerol and chloroform etc.

The compositions suitable for parenteral administration and inspiration are solutions or suspensions of the active ingredient in a suitable medium, e.g. peanut sesame oil, polypropylene glycol or water. The injectable compositions may be administered intramuscularly, intravenously or subcutaneously. The injectable solutions are preferably prepared in an aqueous medium and the pH is adjusted to an appropriate value. The solutions may be prepared, if desired, in the form of physiological saline or glucose solution.

The compositions may be administered also by inhalation when curing asthma, by using the conventional inhalating and nebulizing equipment.

The active ingredient content of the pharmaceutical compositions may vary within a wide range and may be 0.005 to 90%.

The daily dose may vary within a wide range and depends upon the condition the age and weight of the patient and upon the formulated form of the composition and upon the activity of the active ingredient. The daily oral dosage level is generally from 0.05 to 15 mg/kg. while the daily dosage level is generally 0.001 to 5 mg/kg. at once or in several portions a day when administered intravenously or by inspiration.

The above data may vary in both directions according to the prescriptions of the physician.

The further details of the invention are illustrated by the following Examples which are given for illustration and not for limitation.

EXAMPLE 1

To 800 ml of methanol 100.0 g. (0.348 mole) of 9-bromo-6-methyl-4-oxo-6,7,8,9-tetrahydro-4H-pyrido[1,2-a]pyrimidine-3-carboxylic acid and 100 cm$^3$ of aniline are added. The mixture is heated under stirring until a solution is obtained. The solution is cooled to room temperature and stirred for 2–3 days. The precipitated crystals are filtered and washed with methanol. 64.0 g. (61.4%) of 9-(phenyl-amino)-6-methyl-4-oxo-6,7-dihydro-4H-pyrido[1,2-a]pyrimidine-3-carboxylic acid is obtained which melts at 172°–173° C. after recrystallization from methanol.

Analysis for the formula $C_{16}H_{15}N_3O_3$: Calculated: C 64.64%, H 5.09%, N 14.13%. Found: C 64.22%, H 5.08%, N 14.15%.

EXAMPLE 2

To a solution of 0.4 g. (9.22 moles) of sodium hydroxide in 10 ml. of water 2.0 g. (6.15 mmoles) of 9-(phenyl-amino)-6-methyl-4-oxo-6,7-dihydro-4H-pyrido[1,2-a]pyrimidine-3-carboxylic acid ethyl ester are added. The suspension is stirred at 60°–70° C. until a solution is obtained (2–3 hours).

The solution is neutralized with a 10% by W/V aqueous solution of hydrochloric acid solution and treated with decolorizing charcoal. After decolorizing the reaction is acidified with a 10% by W/V aqueous solution of hydrochloric acid and the pH is adjusted to 2. The precipitated crystals are filtered and washed with water.

1.5 g. (81.5%) of 9-(phenyl-amino)-6-methyl-4-oxo-6,7-dihydro-4H-pyrido[1,2-a]pyrimidine-3-carboxylic acid is obtained, melting point: 160°–162° C., the products melts at 172°–173° C. after recrystallization from methanol.

Analysis for the formula $C_{16}H_{15}N_3O_3$: Calculated: C 64.64%, H 5.09%, N 14.13%. Found: C 64.60%, H 5.00%, N 14.11%.

EXAMPLE 3

2.0 g. (6.35 mmoles) of 9-bromo-6-methyl-4-oxo-6,7,8,9-tetrahydro-4H-pyrido[1,2-a]pyrimidine-3-carboxylic acid ethyl ester are dissolved in 6 ml. of methanol and 1.8 ml. of aniline is added. The reaction mixture is allowed to stand for 2 days at room temperature and the solvent is distilled off in vacuo. The residue is taken up in 5 cm$^3$ benzene and the precipitated crystals are filtered. The filtrate is evaporated in vacuo and to the residue 7.6 cm$^3$ of 5% by weight aqueous solution of sodium hydroxide is added.

The mixture is stirred for 3–4 hours at room temperature while a solution is obtained. The solution is neutralized with a 10% by W/V aqueous solution of hydrochloric acid, treated with decolorizing charcoal and the pH is adjusted to 2. The aqueous layer is decanted from the separated oil, the oily part is triturated with some methanol and the crystals are filtered and washed with methanol. 0.8 g. (42.1%) of 9-(phenyl-amino)-6-methyl-4-oxo-6,7-dihydro-4H-pyrido[1,2-a]pyrimidine-3-carboxylic acid is obtained which melts at 171°–172° C. after recrystallization from methanol.

Analysis for the formula $C_{16}H_{15}N_3O_3$: Calculated: C 64.64%, H 5.09%, N 14.13%. Found: C 64.70%, H 5.12%, N 14.20%.

EXAMPLE 4

According to Example 3 but replacing aniline by o-toluidine 0.8 g. (40.1%) 6-methyl-9-[(2-methyl-phenyl)-amino]-4-oxo-6,7-dihydro-4H-pyrido[1,2-a]pyrimidine-3-carboxylic acid is obtained, which melts at 157°–159° C. after recrystallization from methanol.

Analysis for the formula $C_{17}H_{19}N_3O_3$: Calculated: C 65.58%, H 5.50%, N 13.50%. Found: C 65.04%, H 5.60%, N 13.39%.

EXAMPLE 5

40.0 g. (0.127 mole) of 9-bromo-6-methyl-4-oxo-6,7,8,9-tetrahydro-4H-pyrido[1,2-a]pyrimidine-3-carboxylic acid ethyl ester are dissolved in 80 ml. of dimethylsulfoxide and 26 ml. (0.285 mole) of aniline are added. The solution is allowed to stand at room temperature for 3–4 days. The mixture is then diluted with 100 ml. of water, shaken out with 3×50 ml. of benzene. The combined organic layers are dried with calcinated sodium sulfate and evaporated in vacuo. The residue is recrystallized from ethanol and thus 24.5 g. (59.3%) of 9-(phenyl-amino)-6-methyl-4-oxo-6,7-dihydro-4H-pyrido[1,2-a]pyrimidine-3-carboxylic ethyl ester is obtained, melting point: 119°–120° C.

Analysis for the formula $C_{18}H_{19}N_3O_3$: Calculated: C 66.45%, H 5.89%, N 12.91%. Found: C 66.30%, H 5.80%, N 12.83%.

EXAMPLE 6

0.5 g. (2.00 mmoles) of 9-hydroxy-6-methyl-4-oxo-6,7-dihydro-4H-pyrido[1,2-a]pyrimidine-3-carboxylic acid ethyl ester is dissolved in 5 ml. of anhydrous ethanol. To the solution 0.3 g. (3.00 mmoles) of aniline is added and the solution is heated under reflux for 3 hours. The reaction mixture is then cooled and the precipitated crystals are filtered and washed with some ethanol. 0.3 g. (46.1%) of 9-(phenyl-amino)-6-methyl-4-oxo-6,7-dihydro-4H-pyrido[1,2-a]pyrimidine-3-carboxylic acid ethyl ester is obtained, melting point: 119°–120° C.

Analysis for the formula $C_{18}H_{19}N_3O_3$: Calculated: C 66.45%, H 5.89%, N 12.91%. Found: C 65.46%, H 5.90%, N 12.82%.

EXAMPLE 7

10.0 g. (31.83 mmoles) of 9-bromo-6-methyl-4-oxo-6,7,8,9-tetrahydro-4H-pyrido[1,2-a]pyrimidine-3-carboxylic acid ethyl ester are dissolved in 100 ml. anhydrous ethanol. 6.9 ml. (63.66 mmoles) of N-methylaniline are added to the solution, whereafter the reaction mixture is boiled under reflux for 8 hours. When the reaction is completed the solvent is distilled off at reduced pressure. To the residue 100 cm³ 5% by weight aqueous solution of hydrochloric acid is added followed by extraction of the product twice with 30 ml. chloroform. The combined organic layers are dried above calcinated sodium sulfate and evaporated in vacuo. The residue is dissolved in 25 cm³ of methanol and allowed to stand overnight in a refrigerator. The precipitated crystals are filtered and washed with some methanol. 2.8 g. (25.9%) of 9-(N-methyl-anilino)-6-methyl-4-oxo-6,7-dihydro-4H-pyrido[1,2-a]pyrimidine-3-carboxylic acid ethyl ester is obtained which after recrystallization from methanol melts at 131°–133° C.

Analysis for the formula $C_{19}H_{21}N_3O_3$: Calculated: C 67.25%, H 6.23%, N 12.38%. Found: C 67.40%, H 6.35%, N 12.43%.

EXAMPLE 8

2.0 g. (6.97 mmoles) of 9-bromo-6-methyl-4-oxo-6,7,8,9-tetrahydro-4H-pyrido[1,2-a]pyrimidine-3-carboxylic acid and 1.72 g. of p-bromo-aniline are added to 20 cm³ methanol. The mixture is heated under stirring until a solution is obtained. The solution is cooled to room temperature and stirred for 2–3 days. The precipitated crystals are filtered and washed with methanol. 1.7 g. (64.6%) of 9-[(4-bromo-phenyl)-amino]-6-methyl-4-oxo-6,7-dihydro-4H-pyrido[1,2-a]pyrimidine-3-carboxylic acid is obtained which melts at 202°–204° C. after recrystallization from methanol.

Analysis for the formula $C_{16}H_{14}N_3O_3Br$: Calculated: C 51.08%, H 3.75%, N 11.17%, Br 21.24%. Found: C 51.15%, H 3.80%, N 10.90%, Br 21.21%.

EXAMPLE 9

According to Example 1 but replacing 9-bromo-6-methyl-4-oxo-6,7,8,9-tetrahydro-4H-pyrido(1,2-a)pyrimidine-3-carboxylic acid (-)-9-phenyl-amino)-6-methyl-4-oxo-6,7-dihydro-4H-pyrido(1,2-a)pyrimidine-3-carboxylic acid is prepared, melting point: 154°–155° C.; yield: 40%.

Analysis for the formula $C_{16}H_{15}N_3O_3$: Calculated: C 64.64%, H 5.09%, N 14.13%. Found: C 64.51%, H 4.96%, N 14.01%.

EXAMPLES 10 TO 13

2.9 g. (0.01 mole) of 9-bromo-6-methyl-4-oxo-6,7,8,9-tetrahydro-4H-pyrido[1,2-a]pyrimidine-3-carboxylic acid are dissolved in 5 ml. of dimethylsulfoxide. To the solution 0.02 mole of aromatic amine is added (see Table 1). The reaction mixture is allowed to react for three days in an open vessel. 20 ml. of water are then added. The precipitated crystals are washed with water and dried. The crude product is recrystallized from a solvent given in Table 1.

TABLE 1

| No of Example | Starting aniline | Product | Yield (%) | M.p. °C. | Recrystallization solvent | Empirical formula | Elementary analysis Calculated | | found |
|---|---|---|---|---|---|---|---|---|---|
| | | | | | | | C | H | N |
| 10 | p-ethoxy-aniline | 9-(4-ethoxy-anilino)-6-methyl-4-oxo-6,7-dihydro-4H-pyrido[1,2-a]-pyrimidine-3-carboxylic acid | 52 | 210–11 | acetonitrile | $C_{18}H_{19}N_3O_4$ | 63.33 | 5.61 | 12.31 |
| | | | | | | | 63.12 | 5.54 | 12.25 |
| 11 | p-nitro-aniline | 6-methyl-9-(4-nitro-anilino)-4-oxo-6,7-dihydro-4H-pyrido[1,2-a]pyrimidine-3-carboxylic | 20 | 246–47 | dimethyl-formamide | $C_{16}H_{14}N_4O_5$ | 56.14 | 4.12 | 16.36 |
| | | | | | | | 55.99 | 4.08 | 16.29 |

TABLE 1-continued

| No of Example | Starting aniline | Product | Yield (%) | M.p. °C. | Recrystallization solvent | Empirical formula | Elementary analysis Calculated C H N | | | Elementary analysis found C H N | | |
|---|---|---|---|---|---|---|---|---|---|---|---|---|
| | | | | | | | Calculated | | | found | | |
| | | | | | | | C | H | N | C | H | N |
| 12 | aniline | acid 9-anilino-6-methyl-4-oxo-6,7-dihydro-4H-pyrido[1,2-a]pyrimidine-3-carboxylic acid | 57 | 174–75 | methanol | $C_{16}H_{15}N_3O_3$ | 64.64 | 5.09 | 14.13 | 64.52 | 5.00 | 13.98 |
| 13 | p-chloro-aniline | 6-methyl-9-(4-chloro-anilino)-4-oxo-6,7-dihydro-4H-pyrido[1,2-a]pyrimidine-3-carboxylic acid | 96 | 202–03 | acetonitrile | $C_{16}H_{14}N_3O_3Cl$ | 57.92 | 4.25 | 12.67 | 57.72 | 4.30 | 12.90 |

EXAMPLE 14

14.35 g. (0.05 mole) of 9-bromo-6-methyl-4-oxo-6,7,8,9-tetrahydro-4H-pyrido[1,2-a]pyrimidine-3-carboxylic acid are dissolved in 100 ml. of anhydrous chloroform. To the solution 15.0 ml. (0.15 mole) of n-butyl amine are added. The reaction mixture is allowed to stand for 3 days at room temperature, whereafter 70 ml. of water are added. The pH-value of the aqueous layer is adjusted under vigorous stirring to 2 by adding 10% by W/V hydrochloric acid solution. The organic layer is separated and the aqueous layer is shaken out with 2×50 ml. of chloroform. The combined organic layers are dried above calcinated sodium sulfate, finally the solvent is distilled off at reduced pressure. The residue is crystallized from methanol. 4.3 g. (31%) of 9-(n-butyl-amino)-6-methyl-4-oxo-6,7-dihydro-4H-pyrido[1,2-a]pyrimidine-3-carboxylic acid is obtained. Melting point: 13.5°–137° C.

Analysis for the formula $C_{14}H_{19}N_3O_3$: Calculated: C 60.63%, H 6.91%, N 15.15%. Found: C 61.24%, H 7.08%, N 15.06%.

EXAMPLE 15

5.0 g. (14.64 mmoles) of 6-methyl-9-(N-methylanilino)-4-oxo-6,7,8,9-tetrahydro-4H-pyrido[1,2-a]pyrimidine-3-carboxylic acid ethyl ester are dissolved in 100 ml. of chloroform. The solution is heated for 9 hours under reflux and air is bubbled into the reaction mixture. The solvent is distilled off in vacuo. The residue is crystallized from ethanol. 2.9 g. (58.4%) of 6-methyl-9-(N-methyl-anilino)-4-oxo-6,7-dihydro-4H-pyrido[I,2-a]pyrimidine-3-carboxylic acid ethyl ester is obtained which does not give a melting point depression when admixed with the product of Example 7. Melting point: 140°–142° C.

Analysis for the formula $C_{19}H_{21}N_3O_3$: Calculated: C 67.24%, H 6.23%, N 12.38%. Found: C 67.44%, H 6.36%, N 12.23%.

EXAMPLES 16 TO 17

2.9 g. (0.01 mole) of 9-bromo-6-methyl-4-oxo-6,7,8,9-tetrahydro-4H-pyrido[1,2-a]pyrimidine-3-carboxamide are dissolved in 20 ml. of acetonitrile and to the solution 0.025 mole of amine (see Table 2) is added and the mixture is heated for 4–5 hours. The precipitated substance is filtered, washed with water and dried.

TABLE 2

| No. of Example | Starting amine | Product | Yield (%) | M.p. °C. | Recrystallization solvent | Emperical formula | Elementary analysis(%) calculated C H N | | | Elementary analysis(%) found C H N | | |
|---|---|---|---|---|---|---|---|---|---|---|---|---|
| | | | | | | | calculated | | | found | | |
| | | | | | | | C | H | N | C | H | N |
| 16 | benzyl amine | 9-(benzyl-amino)-6-methyl-4-oxo-6,7-dihydro-4H-pyrido-[1,2-a]pyrimidine-3-carboxamide | 43 | 190–92 | — | $C_{17}H_{17}N_4O_2$ | 66.00 | 5.54 | 18.11 | 65.95 | 5.24 | 18.10 |
| 17 | n-butyl-amine | 9-(n-butyl-amino)-6-methyl-4-oxo-6,7-dihydro-4H-pyrido-[1,2-a]pyrimidine-3-carboxamide | 50 | 178–80 | — | $C_{14}H_{19}N_4O_2$ | 61.07 | 6.95 | 20.34 | 61.00 | 6.79 | 20.14 |

EXAMPLE 18

To a solution of 0.4 g. of sodium hydrogen carbonate in 20 ml. of water 1.0 g. (3.34 mmoles) of 9-anilino-6-methyl-4-oxo-6,7,8,9-tetrahydro-4H-pyrido[1,2-a]pyrimidine-3-carboxylic acid is added. The suspension is stirred at 80°–90° C., while air is bubbled through the mixture. The solids are dissolved and the solution is then stirred for half an hour and allowed to cool to room temperature. The pH-value is adjusted to 2 by the addition of a 5% by weight solution of hydrochloric acid. The precipitated crystals are filtered, washed with water and dried. 0.65 g. (65.5%) of 9-anilino-6-methyl-4-oxo-6,7-dihydro-4H-pyrido[1,2-a]pyrimidine-3-carboxylic acid is obtained. Melting point: 152°–154° C. After recrystallization from methanol the product melts at 172°–174° C. The substance when admixed with the product of Example 1 does not show melting point depression.

Analysis for the formula $C_{16}H_{15}N_3O_3$: Calculated: C 64.64%, H 5.09%, N 14.13%. Found: C 64.72%, H 5.22%, N 14.10%.

EXAMPLE 19

2.9 g. (0.01 mole) of (−)-9-bromo-6-methyl-4-oxo-6,7,8,9-tetrahydro-4H-pyrido[1,2-a]pyrimidine-3-carboxylic acid ($[\alpha]_D^{20} = -105°$, c=2, methanol) are dissolved in 5 ml. of dimethyl-sulfoxide and 3.8 g. (0.022 mole) of p-bromo-aniline are added. The solution is allowed to stand for 3 days at room temperature in an open vessel. 20 ml. of methanol are then added to the reaction mixture. The precipitated crystals are then filtered and washed with methanol. 1.7 g. (45.2%) of (−)-9-(4-bromo-anilino)-6-methyl-4-oxo-6,7,8,9-tetrahydro-4H-pyrido[1,2-a]pyrimidine-3-carboxylic acid is obtained. Melting point: 210°–211° C.

Analysis for the formula $C_{16}H_{14}N_3O_3Br$: Calculated: C 51.08%, H 3.75%, N 11.17%, Br 21.24%. Found: C 51.25%, H 3.80%, N 10.90%, Br 21.24%.

EXAMPLE 20

5.0 g. (0.016 mole) of 9-bromo-6-methyl-4-oxo-6,7,8,9-tetrahydro-4H-pyrido[1,2-a]pyrimidine-3-carboxylic acid ethyl ester are dissolved in 50 ml. of ethanol. To the solution 3.5 ml. (0.032 mole) of N-methyl-aniline are added and the reaction mixture is boiled for 8–9 hours in a nitrogen gas atmosphere. 50 ml. or 5% by weight hydrochloric acid solution is then added to the solution and shaken out three times with 25 ml. of dichloromethane. The combined organic layers are dried above calcinated sodium sulfate and evaporated at reduced pressure. The residue is dark oil which crystallizes upon the addition of some methanol. 3.0 g. (55.2%) of 6-methyl-9-(N-methyl-anilino)-4-oxo-6,7,8,9-tetrahydro-4H-pyrido[1,2-a]pyrimidine-3-carboxylic acid ethyl ester are obtained. Melting point: 175°–178° C.

Analysis for the formula $C_{19}H_{23}N_3O_3$: Calculated: C 66.85%, H 6.79%, N 12.30%. Found: C 67.25%, H 6.80%, N 12.16%.

EXAMPLE 21

To a solution of 5 g. of sodium hydroxide in 300 ml. of water 20 g. (58.56 mmoles) of 6-methyl-9-(N-methyl-anilino)-4-oxo-6,7,8,9-tetrahydro-4H-pyrido[1,2-a]pyrimidine-3-carboxylic acid ethyl ester is added. The suspension is stirred for 15 hours at 60°–70° C. The crystals are then filtered and washed with water. The crude product is crystallized from ethanol. 9.0 g. (57.1%) of 6-methyl-9-(N-methyl-anilio)-4-oxo-6,7,8,9-tetrahydro-4H-pyrido[1,2-a]pyrimidine-4-one are obtained, melting point: 188°–189° C.

Analysis for the formula $C_{16}H_{19}N_3O$: Calculated: C 71.35%, H 7.11%, N 15.60%. Found: C 71.69%, H 7.30%, N 15.39%.

EXAMPLE 22

148.7 g. (0.50 mole) of 9-bromo-6-methyl-4-oxo-6,7,8,9-tetrahydro-4H-pyrido[1,2-a]pyrimidine-3-carboxylic acid are dissolved in 250 ml. of acetonitrile and 100 ml. of aniline are further added. The solution is stirred for 2 days in a nitrogen gas atmosphere at room temperature. 1000 ml. of water is added and the mixture is stirred for a further half an hour. The crystals are filtered and washed with water and finally reboiled in 1400 ml. of methanol. 128.8 g. (86.11%) of 9-anilino-6-methyl-4-oxo-6,7,8,9-tetrahydro-4H-pyrido[1,2-a]pyrimidine-3-carboxylic acid are obtained. Melting point: 198°–199° C.

Analysis for the formula $C_{16}H_{17}N_3O_3$: Calculated: C 64.20%, H 5.72%, N 14.04%. Found: C 64.50%, H 5.99%, N 13.81%.

EXAMPLE 23

To a solution of 0.4 g. of sodium hydroxide in 10 ml. of water 1.0 g. (3.34 mmoles) of 9-anilino-6-methyl-4-oxo-6,7,8,9-tetrahydro-4H-pyrido[1,2-a]pyrimidine-3-carboxylic acid is added. The solution is stirred for 5 hours in a hydrogen gas atmosphere at 70°–80° C. The reaction mixture is then cooled to room temperature, the precipitated crystals are filtered and washed with water. 0.4 g. (46.9%) of 9-anilino-6-methyl-6,7,8,9-tetrahydro-4H-pyrido[1,2-a]pyrimidine-4-one is obtained. Melting point: 160°–162° C. The product melts at 165°–167° C. after recrystallization from acetonitrile.

Analysis for the formula $C_{15}H_{17}N_3O$: Calculated: C 70.56%, H 6.71%, N 16.46%. Found: C 70.95%, H 6.82%, N 16.37%.

EXAMPLE 24

1.0 g. (3.48 mmoles) of 9-bromo-6-methyl-4-oxo-6,7,8,9-tetrahydro-4H-pyrido[1,2-a]pyrimidine-3-carboxylic acid is dissolved in 4 ml. of pyridine and the solution is allowed to stand for 3 days at room temperature. The precipitated crystals are filtered and washed with chloroform. 0.75 g. (66.9%) of 1-(6-methyl-4-oxo-6,7,8,9-tetrahydro-4H-pyrido[1,2-a]pyrimidine-9-yl)-pyridinium bromide is obtained. Melting point: 250°–252° C. After recrystallization twice from methanol the melting point is increased to 270°–272° C.

Analysis for the formula $C_{14}H_{16}N_3OBr$: Calculated: C 52.19%, H 5.01%, N 13.04%, Br 24.80%, Found: C 52.16%, H 4.98%, N 12.92%, Br 25.20%.

What we claim is:

1. A compound of the formula:

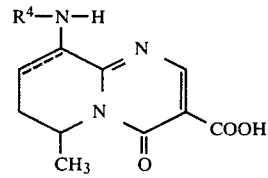

or a pharmaceutically acceptable salt, hydrate, stereoisomer, optically active isomer, geometric isomer, or tautomer thereof wherein the broken line is an optionally present carbon-carbon double bond;

and $R^4$ is phenyl or phenyl substituted by $C_1$ to $C_4$ alkyl, halo, $C_1$ to $C_4$ alkoxy or nitro.

2. A compound of the formula:

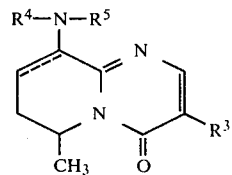

or a pharmaceutically acceptable salt, hydrate, stereoisomer, optically active isomer, geometric isomer, or tautomer thereof wherein the broken line is an optionally present carbon-carbon double bond;

$R^3$ is hydrogen, carboxy, lower alkoxycarbonyl, or carbamoyl;

$R^4$ is phenyl, phenyl substituted by $C_1$ to $C_4$ alkyl, halo, $C_1$ to $C_4$ alkoxy, or nitro, or benzyl; and $R^5$ is hydrogen or $C_1$ to $C_4$ alkyl.

3. A compound of the formula:

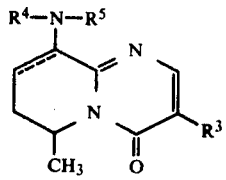

or a pharmaceutically acceptable salt, hydrate, stereoisomer, optically active isomer, geometric isomer or tautomer thereof wherein the broken line is an optionally present carbon-carbon double bond;

$R^3$ is hydrogen, carboxy, lower alkoxycarbonyl or carbamoyl;

$R^4$ is phenyl, naphthyl, phenyl or naphthyl substituted by hydroxy, $C_1$ to $C_4$ alkoxy, nitro, $C_1$ to $C_4$ alkyl, trifluoromethyl, amino or halo, or benzyl; and $R^5$ is hydrogen or $C_1$ to $C_4$ alkyl.

4. The compound defined in claim 2 selected from the group which consists of:

9-(phenyl-amino)-6-methyl-4-oxo-6,7-dihydro-4H-pyrido[1,2-a]pyrimidine-3-carboxylic acid;

6-methyl-9-[(2-methyl-phenyl)-amino]-4-oxo-6,7-dihydro-4H-pyrido-[1,2-a]pyrimidine-3-carboxylic acid;

9-(phenyl-amino)6-methyl-4-oxo-6,7-dihydro-4H-pyrido[1,2-a]pyrimidine-3-carboxylic acid ethyl ester;

9-(N-methyl-anilino)-6-methyl-4-oxo-6,7-dihydro-4H-pyrido[1,2-a]pyrimidine-3-carboxylic acid ethyl ester;

9-[(4-bromo-phenyl)-amino]-6-methyl-4-oxo-6,7-dihydro-4H-pyrido[1,2-a]pyrimidine-3-carboxylic acid;

9-(4-ethoxy-anilino)-6-methyl-4-oxo-6,7-dihydro-4H-pyrido[1,2-a]pyrimidine-3-carboxylic acid;

6-methyl-9-(4-nitro-anilino)-4-oxo-6,7-dihydro-4H-pyrido[1,2-a]pyrimidine-3-carboxylic acid;

6-methyl-9-(N-methyl-anilino)-4-oxo-6,7,8,9-tetrahydro-4H-pyrido[1,2-a]pyrimidine;

9-anilino-6-methyl-6,7,8,9-tetrahydro-4H-pyrido[1,2-a]pyrimidine-4-one; and 9-anilino-6-methyl-4-oxo-6,7,8,9-tetrahydro-4H-pyrido[1,2-a]pyrimidine-3-carboxylic acid or a pharmaceutically acceptable salt, hydrate, stereoisomer, optically active isomer, geometric isomer or tautomer thereof.

5. The compound defined in claim 4 which is 9-phenyl-amino-6-methyl-4-oxo-6,7-dihydro-4H-pyrido[1,2-a]pyrimidine-3-carboxylic acid or an optically active antipode or a pharmaceutically acceptable salt thereof.

6. A method of treatment of an animal subject suffering from asthma, which comprises administering to the subject an effective amount of the compound defined in claim 1 or a pharmaceutically acceptable salt, hydrate, stereoisomer, optically active isomer, geometric isomer, or tautomer thereof.

7. A method of treatment of an animal subject suffering from asthma, which comprises administering to the subject an effective amount of the compound defined in claim 2 or a pharmaceutically acceptable salt, hydrate, stereoisomer, optically active isomer, geometric isomer, or tautomer thereof.

8. A method of treatment of an animal subject suffering from asthma, which comprises administering to the subject an effective amount of the compound defined in claim 3 or a pharmaceutically acceptable salt, hydrate, stereoisomer, optically active isomer, geometric isomer, or tautomer thereof.

* * * * *